United States Patent [19]

Breuer et al.

[11] 4,141,800

[45] Feb. 27, 1979

[54] ELECTROCHEMICAL GAS DETECTOR AND METHOD OF USING SAME

[75] Inventors: Wolfram Breuer; Wolf-Jürgen Becker, both of Leverkusen; Jacques Deprez, Frechen; Eckard Drope, Cologne; Hans-Joachim Schmauch, Blecher, all of Fed. Rep. of Germany

[73] Assignee: Bayer Aktiengesellschaft, Leverkusen, Fed. Rep. of Germany

[21] Appl. No.: 791,126

[22] Filed: Apr. 25, 1977

[30] Foreign Application Priority Data

May 15, 1976 [DE] Fed. Rep. of Germany ....... 2621676

[51] Int. Cl.$^2$ ............................................. G01N 27/46
[52] U.S. Cl. ................................. 204/1 T; 204/195 P; 204/195 S; 55/158; 55/387; 23/232 E; 422/98; 423/210; 423/220; 423/230; 423/239; 423/240
[58] Field of Search ............... 204/1 T, 1 F, 1 B, 1 P, 204/195 R, 195 S, 195 P, 1 N, 1 K, 1 S; 55/158, 387; 73/23; 23/232 E, 254 E; 423/210, 220, 230, 239, 240

[56] References Cited

U.S. PATENT DOCUMENTS

| | | | |
|---|---|---|---|
| 3,857,760 | 12/1974 | Breuer et al. | 204/195 S |
| 3,915,831 | 10/1975 | Riseman et al. | 204/195 P |
| 4,049,503 | 9/1977 | Becker et al. | 204/195 S |

Primary Examiner—T. Tung
Attorney, Agent, or Firm—Sprung, Felfe, Horn, Lynch & Kramer

[57] ABSTRACT

An electrochemical gas detector based on an electrolytic measurement cell having a normally solid organic electrolyte. The gas component to be detected diffuses out of the gas chamber at a three phase border (electrolyte-electrode-gas chamber) and there causes a change in the electrochemical equilibrium. As a result in an outer closing circuit a measurable electrical current is produced. The electrolyte consists of an anhydrous organic gel with a very low vapor pressure. The gas chamber adjacent to the three phase border constitutes a partly sealed cavity, which is in communication with the gas atmosphere to be examined via an absorption filter selectively permeable to the measurement component. The length of the cavity is dimensioned so as to be so short that practically no back diffusion of the measurement component through the filter takes place.

17 Claims, 2 Drawing Figures

ELECTROCHEMICAL GAS DETECTOR AND METHOD OF USING SAME

The invention relates to an electrochemical gas detector for the detection of gas traces based on an electrolytic measurement cell with a normally solid organic electrolyte, in which the gas component to be detected from the gas chamber diffuses to a three phase boundary (electrolyte-electrode-gas chamber) and there brings about a change in the electrochemical equilibrium. As a result there is created in an outer closing circuit an electrical current, the level of which is a value for the gas trace concentration.

The monitoring of emissions in the atmosphere is only possible if the physical and material changes in the air can be quantitatively determined. To achieve this, the exact determination of numerous components is necessary. Many of these impurities must be detected at high dilutions. The present invention is concerned with the detection and measurement of such gas traces, both in the external air and in enclosed rooms (living rooms, workplaces etc.). A further area of application is the determination of gas traces in gas and waste gas flows of manufacturing concerns in the chemical industry.

In gas trace analysis electrochemical methods are frequently used. For this purpose the measurement electrode of a galvanic element is brought into contact with the gas to be examined. By so doing an electrical current is produced which is proportional to the concentration of the measurement component. The measurement element is generally in the form of a through-flow measurement cell, in which the gas to be examined flows past the measurement electrode of the galvanic element. The flow is maintained by means of suitable transport devices. As the selectivity of such gas detectors is generally low, a suitable filter is arranged before the through-flow measurement cell to increase the selectivity. The requirements of such filters are for example described in VDI guideline 2451, page 4, 1968. Such filters in general depend on the chemical sorption of the interference components, i.e. the disruptive gas components are bonded in the filter material by chemical reactions. The filter material consists of amongst other things chemically treated granulate or fibre material. In the chamical treatment, the granulate or the fibres are provided with a coating of a substance which undergoes a chemical reaction with the disruptive components to be filtered out. The fibre or granulate fills the entire cross-section of a tube which is placed before the measurement cell as a filter unit.

Because of the forcible transport, the effectiveness of the filter can be increased by correspondingly long flow paths. The resultant relatively large dimensions of such filters have no adverse effect. As the through-flow is always maintained constant by the forcible transport, variations of the flow resistance, e.g. by gradual clogging of the filter, in the first instance have no influence on the measurement effect. By the appropriate design of the filter and suitable choice of the flow speed, the residence time in the filter can be simply adapted to the particular measurement problem.

In this respect gas trace measurement devices based on diffusion measurement heads are substantially more problematical. Thus filter systems which are suitable for through-flow devices cannot readily be transferred to devices having diffusion measurement heads. In detail, the following conditions have to be fulfilled:

1. By arranging a filter before the diffusion measurement head of a gas analysis unit, the sensitivity is reduced. This loss of sensitivity must be kept as low as possible.
2. The response time and regeneration behaviour of the diffusion measurement head is lengthened by the filter. Such an extension of the time constants is almost always undesirable.
3. Since the gas component to be measured by diffusion passes through the filter, the filter must remain constant in its diffusion behaviour over a long time. Changes in the diffusion behaviour would simulate sensitivity changes.
4. The electrolyte in the electrochemical measurement element has a final vapour pressure. These vapours are also sorbed in the filter and cause interference in respect of the absorption of the components to be filtered out.
5. Conversely, a vapour pressure originating from the filter interferes with the electrochemical equilibrium at the electrolyte measurement cell. As a result defective measurement can be caused. The inherent vapour pressure of the filter must therefore be very small.
6. The measurement component must pass the filter chemically unchanged.
7. The problem frequently occurs that the measurement component must be detected in an interference background which is several times higher. As a result the filter must also absorb high concentrations of interference components.
8. In gas warning devices based on diffusion measurement heads, miniaturisation is striven for. It is therefore important that the filter should have small dimensions. As a rule this requirement can only be reconciled with difficulty with a high degree of long term stability.

When gas trace measurement devices are used in manufacturing concerns, instances may occur in which the diffusion measurement cell receives directly the flow of the measurement gas. In such cases the device normally simulates a high concentration. In order to achieve correct information, it is desirable that the measurement effect should be independent from the flow direction and speed. Otherwise the measurement result would be dependent on the position of the measurement head in relation to the direction of flow. However when gas trace measurement devices are used in the emission area, the concentration is not the important value, but rather the emission flow density is of interest (cf. VDI guideline 2450, page 1); i.e., the collision rate (particles per unit of area and time) of the component to be measured. In this process the flow direction and speed play an important role.

The object of the invention therefore is to provide an electrochemical gas detector having a diffusion measurement head to improve the selectivity. In so doing the above specified conditions must be taken into account.

According to the invention, there is provided an electrochemical gas detector for the detection of gas traces, comprising an electrolytic measurement cell comprising an anhydrous organic gel electrolyte, which at temperatures up to 60° C. has a vapour pressure of less than 1 Torr, and a pair of electrodes, the cell being arranged in a housing forming a cavity through which the component to be detected diffuses to a three-phase boundary formed by the atmosphere in the cavity, an electrode and the electrolyte, whereby a current is produced in an electrical circuit connecting the two electrodes, the cavity being in communication with the exterior of the housing via a sorption filter, the distance between the filter and the three-phase boundary being so short that substantially no back diffusion of the component to be detected through the filter takes place. In such an arrangement of the measurement head, the molecules of the gas to be measured diffuse through the filter, subsequently through the cavity between filter and three-phase boundary and are dissolved at the three-phase boundary. The three-phase boundary thus forms a sink for the incoming gas molecules. Under equilibrium conditions, a concentration gradient is produced which determines the diffusion of the measurement gas at the three-phase boundary. As the cavity length increases, the concentration gradient through the filter decreases markedly. Accordingly, the diffusion flow of the measurement component to the three-phase boundary decreases. This represents a corresponding loss of sensitivity. It has proved that for a cavity length of 0.5 to 5 mm, practically no losses occur (less than 10%). The maximum permissible cavity dimensions depend on the diffusion properties of the filters used. The smaller the diffusion coefficient of the filter material, the longer the cavity can be. However in practice the above specified cavity length of 5 mm is not exceeded. Preferably the cavity length is from 1 to 2 mm.

The filter consists usefully of a porous body, in which one or more reactants are present in the solid phase and in finely divided form, which react chemically with the interference components and as a result are sorbed in the porous body. Advantageously the porous body consists of a single or multi-layer membrane of an inert material. Such porous bodies can for example be produced by sintering. According to a further development of the invention the porous body consists of several membrane layers in which different reaction partners are incorporated.

Special combinations of gel electrolytes with individually adapted filters for the detection of specific measurement components are described in the subclaims.

The invention permits the achievement of the following advantages. For the first time a diffusion measurement head has been provided based on an electrochemical measurement cell which substantially fulfills the above specified requirements.

1. No significant loss of sensitivity occurs. It has been possible to ascertain this by means of comparative measurements for a measurement element with and without a filter.
2. The life of a diffusion measurement head according to the invention under conditions such as are present in emission measurement is in the order of magnitude of half a year. During this time no serious losses of sensitivity or changes of the characteristic time behaviour occurred. It can therefore be assumed that the filter cell combination according to the invention has the long term stability absolutely necessary for alarm transmitters. Wind tunnel tests have led to the result that by the corresponding adjustment of the diffusion behaviour and choice of the filter geometry (filter thickness) the sensitivity of the diffusion measurement head according to the invention up to a flow speed of 1 metre per second is virtually independent of the flow direction and the value of the flow speed. Thus devices according to the invention can also be used in flowing media, without the concentration measurement being falsified. On the other hand the diffusion behaviour and the filter thickness can be adjusted so that the diffusion measurement head determines the emission flow density virtually without falsification.

TABLE I sorption behavior of support materials

| Support \ Component | $H_2S$ | $SO_2$ | $NO_2$ | $COCl_2$ |
|---|---|---|---|---|
| Glass fibre paper | ++ | + | + | + |
| Cellulose fibre paper | − | − | − − | − |
| Silver netting 3-layer | − | ++ | + | + |
| Silver netting 3-layer annealed at 900° for 0.5h | − − | − | − | − − |
| Glass frit | ++ | ++ | ++ | + |

++ no noticeable sorption
+ low sorption
− high sorption
− − total sorption
f carrier gas with 60% rel. humidity
t dry carrier gas Table 1 lists various examples for porous bodies as support materials for the sorption filter. It can be seen that various materials already display a strong sorption for the gases under examination: hydrogen sulphide, sulphur dioxide, nitrogen dioxide and phosgene. In this arrangement the high specific surface conditioned by the porosity is of decisive importance. Such supports have the following advantages:

(a) The reagent can be applied on the support in defined distribution.
(b) Only the surface of the support needs to be coated.
(c) The size and structure of the surface of the reagent proportion in the filter can be varied in any desired manner by the suitable choice of the support. The surface having been treated once with the reagent is little affected by the mechanical stressing of the filter.
(d) The filter mass can be brought into various desired shapes. Thus the form and size of the support can be adapted to the specific requirements of the measurement problem.
(e) The often narrow tolerances of the mixing ratios with filters having mixing reagents can often be observed better with the use of these supports than with mixtures of the reagents alone.

TABLE 2 sorption behaviour of reagents

| Reagent \ Gas component | $H_2S$ | $SO_2$ | $NO_2$ | $COCl_2$ | $Cl_2$ |
|---|---|---|---|---|---|
| Phenol-2.4.-disulphonic acid (pure, granulated) | ++ | + | − | − | − |
| Napthylamine-(2)-disulphonic acid (pure, granulated) | ++ | + | − | ++ | − |
| NaI/Na$_2$S$_2$O$_3$ on quartz wool | + | + | − − | + | − − |
| lead acetate on quartz wool | − − | − | + | −f +t | − |
| Ag$_2$SO$_4$/KHSO$_4$ on Ag-wadding K$_2$Cr$_2$O$_7$/H$_2$SO$_4$ | − − | ++ | ++ | ++ | − |

TABLE 2-continued sorption behaviour of reagents

| Reagent | Gas component | | | | |
|---|---|---|---|---|---|
| | $H_2S$ | $SO_2$ | $NO_2$ | $COCl_2$ | $Cl_2$ |
| on quartz wool | − | − − | + + | + + | + |

See table I for meanings of symbols

Table 2 gives information on the selection of suitable reagents for the sorption filter. The gases hydrogen sulphide, sulphur dioxide, nitrogen dioxide, phosgene and chlorine were examined.

Figure 1:
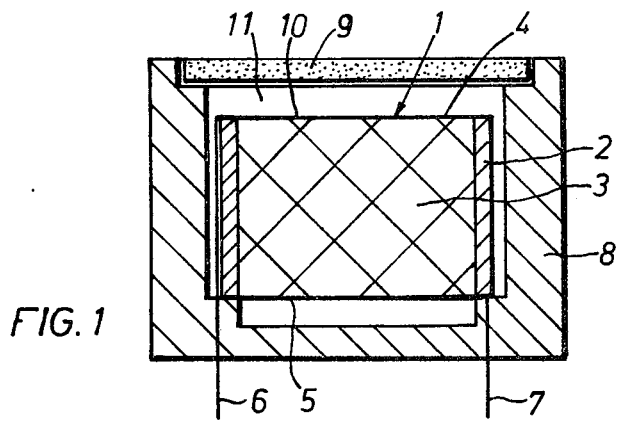
FIG. 1 shows a schematic representation of a diffusion measurement head for the detection of gas traces.

FIG. 1 shows in principle the construction of a diffusion measurement head. The heart of the diffusion measurement head is the electrochemical measuring element 1. It consists of a gel electrolyte 3 embedded in a plastics ring 2, the electrolyte being in contact on either side with the electrodes 4 and 5. The two electrodes 4 and 5 are connected to two terminals 6 and 7. The terminals lead to a direct current amplifier with a low impedance input for the amplification of the current produced by the gel cell 1.

The measuring element 1 is located in a cylindrical plastics housing 8 which is sealed on one side. The measurement cell is sealed from the outside by a disc-shaped sorption filter 9. Between the sorption filter 9 and the three-phase boundary 10 responsible for the electrochemical reaction between gas chamber, electrode 4 and electrolyte 3 there is located a cavity 11 having a length L of approximately 1 mm. The gas to be investigated diffuses from the outer chamber through the sorption filter 9, then through the cavity 11 and is dissolved at the three-phase boundary 10 in the electrolyte 3. A current is produced by the electrochemical reaction of the measurement component at the three-phase boundary 10, which can be measured in the outer closing circuit at the terminals 6 and 7. The electrolyte 3 consists of an anhydrous-organic gel, which is obtained by the effect of an organic solvent on a synthetic polymer. Because of the diffusion interaction with the sorption filter 9, only those gel systems are suitable which have a low vapour pressure. This avoids the possibility of the sorption filter 9 changing chemically with time on account of the vapours issuing from the electrolyte. Preferably a gel is used in accordance with claim 1.

Suitable solvents for the polymer include preferably organic compounds which contain a carbonyl, alkoxyl, hydroxyl or a phosphoric acid ester group. Suitable polymers include homo- or copolymers of olefinically unsaturated compounds, in particular of monovinyl or monovinylidene monomers. The production of the gel electrolytes and their properties have already been described in detail in U.S. Pat. No. 4,049,503. For this reason it is not necessary at this point to include a more detailed description. The production of the sorption filters 9 and their properties and explained further below.

Figure 2:
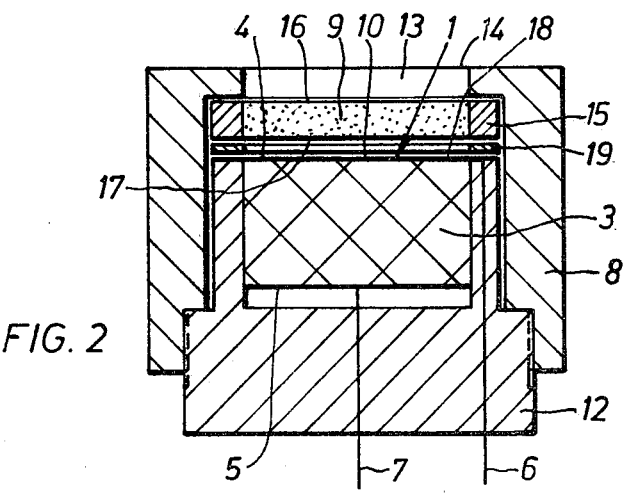
FIG. 2 shows a special embodiment of a diffusion measurement head for determining nitrous gases in motor vehicle exhaust gases.

FIG. 2 shows a diffusion measurement head for determining nitrous gases in motor vehicle exhaust gases. The goal of this development was the measurement of nitrous gases in motor vehicle exhaust gases in a measurement range up to 100 ppm. The measurement cell was intended to fulfill the following requirements in respect of its properties:

(a) It should be as manageable, uncomplicated and maintenance free as possible.

(b) A long service life must be guaranteed.

(c) The measurement cell should be insensitive to water vapour, as the proportion of water vapour in motor vehicle exhaust gases is relatively high.

The measurement element 1 in the diffusion measurement head according to FIG. 2 consists of a hollow cylinder 8, constituting the outer casing, and a screw insert 12, in which the measurement element 1 is embedded and which is screwed from behind into the hollow cylinder 8. At the front of the hollow cylinder 8 there is located the inlet opening 13 for the waste gas having a diameter of approximately 3 cm. This inlet opening 13 is protected with a layer 14 of glass fibre paper against oil and water drops. Inside the hollow cylinder 8 a sorption filter 9 is incorporated between the inlet opening 13 and the three phase border 10 of the gel electrolyte 3. Between the filter 9 and the three phase border 10 there remains a cavity 11 having a gap length of 1 to 2 mm. The sorption filter 9 is enclosed in a ring 15. On the outside of the sorption filter 9 there is a PTFE film 16 which is from 5 to 7.5 μm thick. The inside is sealed with a glass fibre paper membrane 17. The actual filter material is located between the two membranes 16 and 17. Its composition is described further below. Here it has the task of oxidising nitrogen monoxide to nitrogen dioxide.

The filter can easily be exchanged. For this purpose the screw insert 12 has only to be screwed out. The screw insert 12 carries the measurement element 1, consisting of the measurement electrode 4, the gel electrolyte 3 and the counter electrode 5. The electrodes 4 and 5 are connected to the terminals 7 and 6. A 5 to 7.5 μm thick PTFE film 18 is laid over the three phase boundary 10 and secured on to the edge of the screw insert 12. Between the filter ring 15 and the screw insert 12 with the film 18 there is inserted a spacer ring 19, to avoid damage to the film 18. This also determines the cavity length L. A commercial directed current amplifier can be used as a measurement amplifier being connected to the terminals 6 and 7.

Embodiments for the production of sorption filters and the detection of specific gas components.

1. Measurement of $H_2S$.

Glass fibre paper having a diameter of 12.5 cm is dipped into a solution of 1 part by weight of 3-hydroxydiphenylamine (HDPA) and 4 parts by weight benzene. At approximately 70° the benzene is boiled out for half an hour with a reflux condenser. After decanting the excess solution the support thus prepared is dried with purified air. Subsequently the excess reagent is driven off at approximately 200°.

Such a filter absorbs nitrogen dioxide up to almost 100% in the concentration range of 0 to 10 ppm over many hours. HCl-gas is also quantitatively absorbed. The absorption capacity for chlorine is lower, sulphur dioxide and phosgene are only partially absorbed. The filter is permeable to hydrogen sulphide. Since the filter contains no liquid components, the vapour pressure is negligibly low. The HDPA is present in the glass fibre paper in solid phase and finely distributed form. To protect the filter the two surfaces can be covered before incorporation into the diffusion measurement head with course mesh sieves.

For the detection of hydrogen sulphide, this filter is combined according to FIG. 1 with a measurement element in which the gel electrolyte consists of the polymer polymethylmethacrylate, of the solvent propylene carbonate, with the electrolyte additives sodium benzoate and benzoic acid and is doped with iron (III) sulphate.

2. Measurement of phosgene

A sorption filter suitable for phosgene measurement also consists of glass fibre paper, impregnated with HPDA. The filter is produced as described in Example 1. Subsequently, by means of an additional treatment of the glass fibre paper with 1n-$H_2SO_4$ a reduction of the phosgene adsorption is achieved. A filter thus produced is for the measurement of phosgene traces combined with a filter B which is produced in the following way.

A glass fibre paper membrane having a diameter of 12.5 cm is dipped in a 20% aqueous solution of potassium bisulphate, saturated with silver sulphate, and carefully boiled up for half an hour. After decanting the excess solution, the glass fibre paper thus wetted is dried with purified air. The filter B produced in this way absorbs quantitatively hydrogen sulphide, hydrochloric acid vapours and ammonia, while phosgene is not substantially influenced. For this reason the filter B is suitable as an additional filter for the measurement of phosgene.

This filter combination is again used in the measurement head according to FIG. 1 (soprtion filter 9). The electrolyte of the measurement element 1 has the same composition as described in Example 1. The electrodes 4 and 5 as in the measurement head for the detection of hydrogen sulphide consist of silver.

3. Measurement of nitrogen dixoide

The starting material used for the production of the sorption filter is chromosorb P naw (30–60) of Messrs. Johns Manville. This material is a kieselguhr in compact form, which is also used for purposes of gas chromatography. 1 g potassium bichromate and 1 g 96% sulphuric acid are dissolved in 200 ml water and made into a paste with 10 g chromosorb. At a temperature below 100° C. the water is evaporated at reduced pressure in a rotation evaporator. In this process the reagent mixture is precipitated evenly on the chromosorb.

This filter material has the property that it oxidises quantitatively NO to $NO_2$. Hydrogen sulphide and sulphur dioxide are absorbed. Phosgene, chlorine and hydrochloric acid vapours are little influenced. Such a filter was used in the device described in FIG. 2 for the measure of nitrous gases in motor vehicle exhaust gases. The gel electrolyte in the measurement element has the same composition as in Examples 1 and 2. The electrodes 4 and 5 in this case consist of carbon or gold.

If nitrogen dioxide is to be measured against a background of hydrogen sulphide, then in addition the filter B described in Example 2 is arranged in front. As already described this filter is constructed on the basis of potassium bisulphate and silver sulphate. The glass fibre paper in the filter pipe B can also be replaced by silver netting.

We claim:

1. In an electrochemical gas detector for the detection of gas traces, means defining a gas chamber in communication with the atmosphere to be detected and an electrolytic measurement cell having a normally solid organic electrolyte adjacent to the gas chamber along a three phase boundary and electrodes on opposite sides thereof and wherein the gas component to be detected diffuses out of the gas chamber to the three-phase boundary to effect a change in the electrochemical equilibrium resulting in a measurable electrical current in the electrodes, wherein the electrolyte comprises an anhydrous organic gel, which at temperatures of up to 60° has a vapor pressure of less than 1 Torr, and wherein the means defining the gas chamber comprises a partly sealed cavity and a sorption filter through which the gas chamber is in communication with the atmosphere to be detected, the filter being selectively permeable to the desired gas component to be detected with respect to the detected gas atmosphere, and spaced a given distance from the three phase boundary so as to be sufficiently close thereto to substantially prevent back diffusion of the desired gas component through the filter.

2. In the electrochemical gas detector according to claim 1, wherein the given distance is 0.5 to 5 mm.

3. In the electrochemical gas detector according to claim 2, wherein the given distance is 1 to 2 mm.

4. In the electrochemical gas detector according to claim 1, wherein the filter comprises a porous body, in which at least one reaction partner is present in solid phase and in finely distributed form, and which reacts chemically with the interference components and thus are absorbed in the porous body.

5. In the electrochemical gas detector according to claim 4, wherein the porous body comprises at least one membrane layer of an inert material.

6. In the elctrochemical gas detector according to claim 5, wherein the porous body includes a plurality of membrane layers and different reaction partners are incorporated in the individual membrane layers.

7. In the electrochemical gas detector for the detection of phosgene according to claim 6, wherein the electrodes comprise silver, the gel electrolyte comprises the polymer polymethylmethacrylate of the solvent propylene carbonate with the electrolyte additives sodium benzoate and benzoic acid and is doped with iron (III) sulphate and a part of the multilayer porous body contains 3-hydroxydiphenylamine treated with sulphuric acid and another part contains potassium bisulphate and silver sulphate.

8. In the electrochemical gas detector according to claim 7, wherein the porous body additionally contains metallic silver.

9. In the electrochemical gas detector for the detection of hydrogen sulphide according to claim 4, wherein the electrodes comprise silver, and the gel electrolyte comprises the polymer polymethylmethacrylate, the solvent propylene carbonate, the electrolyte additives sodium benzoate and benzoic acid and is doped with iron (III) sulphate and the reaction partner distributed in the porous body for the interference component is 3-hydroxydiphenylamine.

10. In the electrochemical gas detector for the detection of nitrogen dioxide according to claim 4, wherein one electrode comprises carbon and the other comprises carbon or gold, the gel electrolyte comprises the polymer polymethylmethacrylate, the solvent propylene carbonate, the electrolyte additives sodium benzoate and benzoic acid and is doped with iron (III) sulphate and in that potassium bisulphate and silver sulphate are incorporated in the porous body.

11. In the electrochemical gas detector according to claim 10, wherein the porous body additionally contains metallic silver.

12. In a process for the electrochemical detection of gas traces wherein the improvement comprises:
(a) providing a partly sealed gas chamber in communication with the atmosphere to be detected through a sorption filter which is selectively permeable to the desired gas component to be detected;
(b) diffusing the gas from the gas chamber to a normally solid organic electrolyte at a three phase boundary and spacing the boundary a given distance sufficiently short from the filter so as to substantially prevent back diffusion of the desired gas component through the filter, the electrolyte comprising an anhydrous organic gel which at temperatures up to 60° has a vapor pressure of less then 1 Torr;
(c) applying a measurable current produced as a result of the change in electrochemical equilibrium by step (b) to a measuring device by providing electrodes at opposite ends of the electrolyte.

13. In the process according to claim 12, comprising spacing the filter from the boundary from 0.5 to 5 mm.

14. In the process according to claim 13, comprising spacing the filter from the boundary 1 to 2 mm.

15. In the process according to claim 12, comprising providing a porous body for the filter having at least one reaction partner in solid phase and in finely distributed form and which reacts chemically with the interference components and are thus absorbed in the porous body.

16. In the process according to claim 15 comprising providing a porous body comprising at least one membrane layer of inert material.

17. In the process according to claim 16, comprising providing different reaction partners in the individual membrane layers.

* * * * *